(12) United States Patent
Heckerman

(10) Patent No.: US 11,364,140 B2
(45) Date of Patent: Jun. 21, 2022

(54) FEMALE URINE DEVICE

(71) Applicant: Outstanding Innovations, LLC, Kalispell, MT (US)

(72) Inventor: Brad B. Heckerman, Kalispell, MT (US)

(73) Assignee: Outstanding Innovations, LLC, Kalispell, MT (US)

( * ) Notice: Subject to any disclaimer, the term of this patent is extended or adjusted under 35 U.S.C. 154(b) by 0 days.

(21) Appl. No.: 17/185,511

(22) Filed: Feb. 25, 2021

(65) Prior Publication Data

US 2021/0177644 A1 Jun. 17, 2021

Related U.S. Application Data

(63) Continuation-in-part of application No. PCT/US2019/049520, filed on Sep. 4, 2019, which is a continuation of application No. 16/120,552, filed on Sep. 4, 2018, now Pat. No. 10,568,756.

(51) Int. Cl.
*A61F 5/455* (2006.01)

(52) U.S. Cl.
CPC .......... *A61F 5/4556* (2013.01); *A61F 5/4553* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,964,111 A | * | 6/1976 | Packer | A61F 5/4556 604/327 |
| 3,995,329 A | * | 12/1976 | Williams | A61F 5/455 4/144.3 |
| 4,023,216 A | * | 5/1977 | Li | A61F 5/4556 4/144.1 |
| 4,528,703 A | * | 7/1985 | Kraus | A61F 5/4556 604/350 |
| 4,531,245 A | * | 7/1985 | Lowd | A61G 9/006 604/347 |
| 4,769,858 A | * | 9/1988 | Gamm | A61G 9/006 215/384 |
| 5,318,498 A | * | 6/1994 | Jones | E03D 13/002 493/158 |
| D356,865 S | | 3/1995 | Ivie | |
| 5,408,703 A | * | 4/1995 | Cicio | A61G 9/00 4/144.2 |
| 5,743,948 A | | 4/1998 | Cicio | |

(Continued)

FOREIGN PATENT DOCUMENTS

| | | |
|---|---|---|
| AU | 8089682 | 9/1982 |
| EP | 0073203 | 3/1983 |

(Continued)

*Primary Examiner* — Guy K Townsend
(74) *Attorney, Agent, or Firm* — Heslin Rothenberg Farley & Mesiti PC

(57) ABSTRACT

A female urine device includes a shell portion and a spout portion. The shell portion includes a bottom wall, a first sidewall, a second sidewall and a rear wall integrally connected to define a trough shaped inner chamber. A forward opening is defined by forward ends of the walls. An upper rim is defined by upper ends of the walls. The spout portion extends forward from the forward opening of the shell portion. A portion of the female urine device is phosphorescent.

9 Claims, 8 Drawing Sheets

(56) References Cited

U.S. PATENT DOCUMENTS

| | | | |
|---|---|---|---|
| 5,893,176 A | 4/1999 | Magiera et al. | |
| 5,956,782 A * | 9/1999 | Olguin | A47K 11/12 |
| | | | 4/144.1 |
| 5,966,748 A | 10/1999 | Young et al. | |
| 6,327,716 B1 * | 12/2001 | Kaus | A61F 5/4556 |
| | | | 4/144.4 |
| 6,434,757 B1 * | 8/2002 | Filsouf | A61F 5/4556 |
| | | | 4/144.1 |
| 6,505,355 B1 * | 1/2003 | Mutke | A61F 5/4408 |
| | | | 4/144.1 |
| 6,547,771 B2 | 4/2003 | Robertson et al. | |
| 7,181,781 B1 * | 2/2007 | Trabold | A61F 5/455 |
| | | | 4/144.1 |
| D577,435 S | 9/2008 | Ivie et al. | |
| 8,221,369 B2 | 7/2012 | Parks et al. | |
| 8,235,956 B2 | 8/2012 | Block | |
| 9,888,337 B1 * | 2/2018 | Zalewski | H02N 11/002 |
| 9,911,290 B1 * | 3/2018 | Zalewski | G06Q 30/0633 |
| 10,197,430 B2 * | 2/2019 | Goldsmith | E03C 1/281 |
| 10,568,756 B1 * | 2/2020 | Heckerman | A61F 5/4556 |
| 2001/0041882 A1 * | 11/2001 | Brink | A61F 5/4556 |
| | | | 604/544 |
| 2002/0193762 A1 * | 12/2002 | Suydam | A61G 9/006 |
| | | | 604/327 |
| 2003/0056283 A1 * | 3/2003 | Wang | A61F 5/4556 |
| | | | 4/144.4 |
| 2009/0056003 A1 * | 3/2009 | Ivie | A61F 5/4556 |
| | | | 4/144.3 |
| 2011/0028944 A1 | 2/2011 | Chiu et al. | |
| 2012/0210502 A1 * | 8/2012 | Baham | A61F 5/4556 |
| | | | 4/144.3 |
| 2015/0135423 A1 * | 5/2015 | Sharpe | A61F 5/455 |
| | | | 4/471 |
| 2015/0204710 A1 * | 7/2015 | Goldsmith | G08B 21/20 |
| | | | 4/144.2 |
| 2018/0299433 A1 * | 10/2018 | Dahl | G01N 1/10 |

FOREIGN PATENT DOCUMENTS

| | | |
|---|---|---|
| FR | 8104021 | 9/1982 |
| IT | 1149781 | 12/1986 |
| WO | 8202831 | 9/1982 |

* cited by examiner

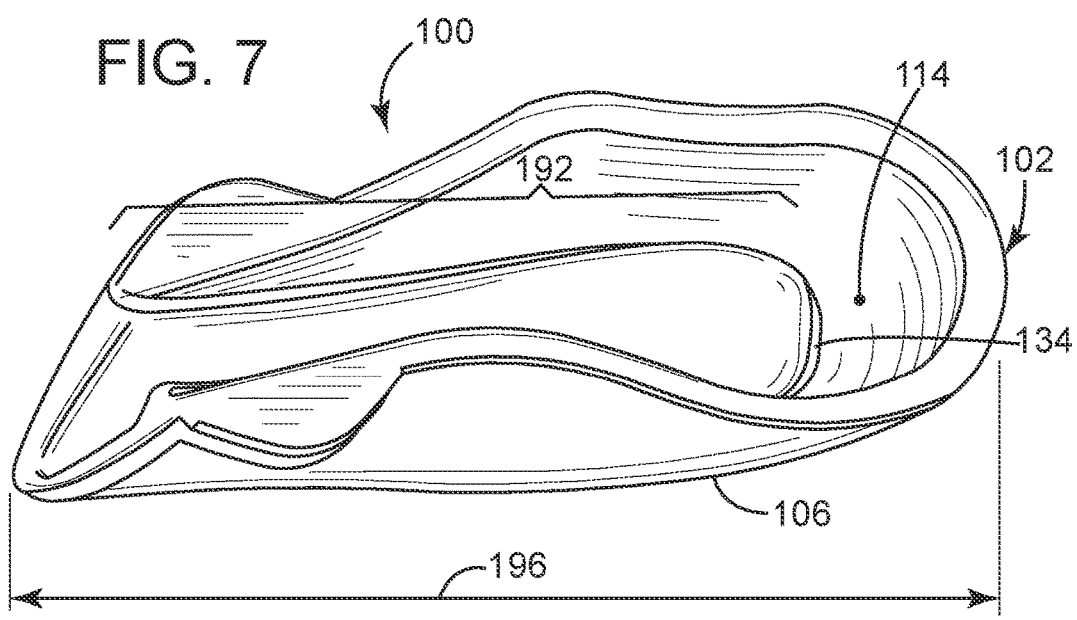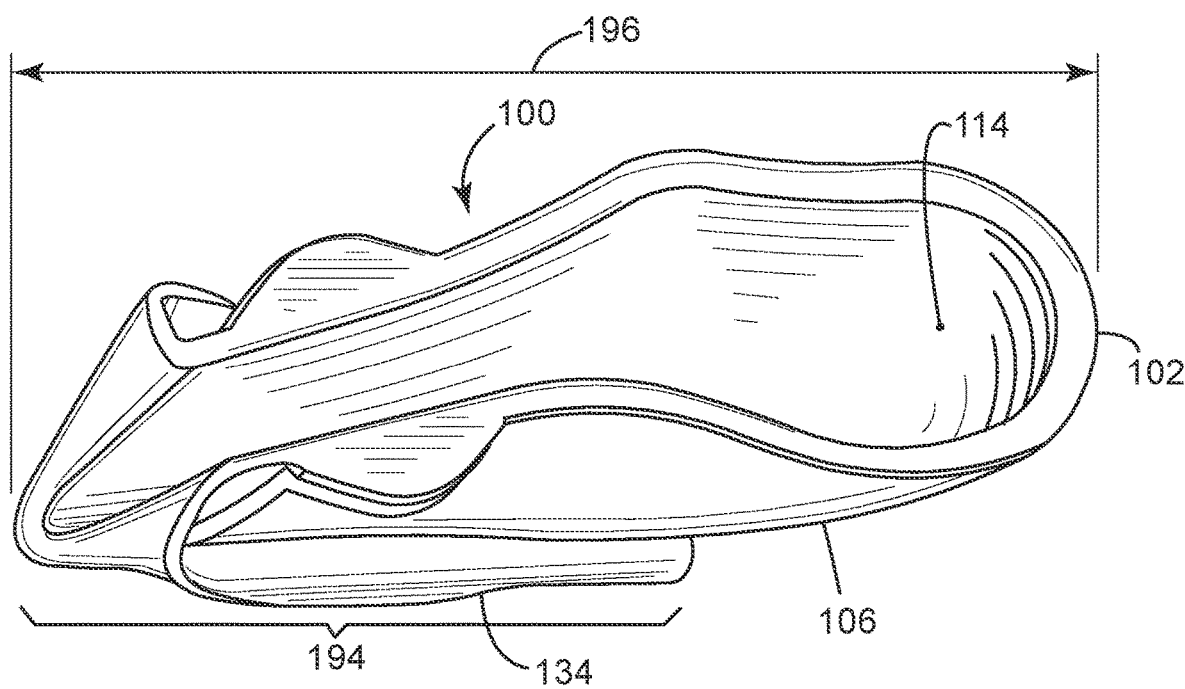

FIG. 10A

202 — Providing a base material for a shell portion and a spout portion of a female urine device.

204 — Adding phosphorescent material to the base material. The phosphorescent material may be composed of at least one of phosphor, zinc sulfide, strontium aluminum, europium or dysprosium.

206 — Thermal molding the base material to form a female urine device, wherein the female urine device includes a shell portion and a spout portion.

The shell portion includes a bottom wall, a first sidewall, a second sidewall and a rear wall integrally connected to define a trough shaped inner chamber. The shell portion also includes a forward opening defined by forward ends of the walls and an upper rim defined by upper ends of the walls.

The spout portion extends forward from the forward opening of the shell portion.

A portion of the female urine device is phosphorescent. The phosphorescent portion may be the spout portion.

FIG. 10B

208 — The phosphorescent material may be in pellet or powder form and may be added to the base material prior to thermally molding the base material to form the female urine device, or the phosphorescent material may be painted onto the female urine device after the female urine device has been thermally molded.

210 — The phosphorescent material may be blended into the base material in a range of between 1 to 25 percent of the base material by weight or in a range of between 3 to 12 percent of the base material by weight.

FEMALE URINE DEVICE

CROSS REFERENCE TO RELATED APPLICATION

This application claims priority benefit of U.S. non-provisional patent application Ser. No. 16/120,552 filed Sep. 4, 2018 and international patent application No. PCT/US2019/049520 filed Sep. 4, 2019, both of which are incorporated herein by reference in their entirety.

TECHNICAL FIELD

The present disclosure relates to female urine devices. More specifically, the disclosure relates to female urine devices which enable a female to urinate while standing.

BACKGROUND

In order to urinate, a female typically must disrobe and sit or squat. However, on many occasions, sitting or squatting to urinate is inconvenient or difficult to do. For example, when hiking over rough outdoor terrain, disrobing may unnecessarily expose a female to harsh weather conditions such as cold wind, snow and heavy rain, or to insects such as mosquitos and black flies. Additionally, disrobing and squatting can be problematic for a female in outdoor public areas, such as parks, which often do not have adequate restroom facilities. In the event there are public restrooms or toilets, many may be dirty and unsanitary. Moreover, certain medical conditions may compound the problem by making it difficult or painful to squat or sit.

Prior art female urine devices which allow a female to urinate while standing (i.e., stand-to-pee devices) may help to alleviate the problem. However, such devices often have several design limitations. For example, prior art female urine devices may leak during urination if not properly positioned and sealed against a female's anatomy.

Often such prior art devices are made of rigid materials throughout to prevent collapsing, and therefore leaking, during use. However, such rigid devices may require an uncomfortable amount of pressure against the female's body in order to seal and prevent leakage. Alternatively, if the prior art device is made of a soft or flexible material, the devices may inadvertently collapse during use when a sealing pressure is applied.

Additionally, such prior art urine devices may be too bulky or too long to conveniently or inconspicuously carry around. This is especially the case when the prior art device is composed of a rigid material throughout.

Further, if the prior art devices are made compact for purposes of easy storage and transport, they may not direct the discharging urine far enough away from a female's body to prevent splashing on one's body or clothing. Such prior art devices may require the female to substantially disrobe to prevent undesirable splashing on one's clothing, which defeats the purpose of a stand-to-pee device.

Additionally, it is often difficult to visualize a prior art urine device because of the lack of light in the area where the user is utilizing the urine device. This leads to inability to see and/or direct the urine flow which makes use of the device difficult.

Accordingly, there is a need for a female urine device that enables a female to conveniently stand during urination without having to disrobe to prevent splashing on one's clothing. Further, there is a need for such a device to be compact enough to easily carry and inconspicuously conceal when not in use, yet long enough to direct discharging urine well away from the body when in use. Moreover, there is a need for a female urine device to be easily and comfortably positioned and sealed against a female's anatomy to greatly reduce the possibility of leakage during use, yet rigid enough to prevent collapsing during use. Further there is a need to be able to see the female urine device in low light conditions and to be able to see and/or direct the urine flow when in use.

BRIEF DESCRIPTION

The present disclosure offers advantages and alternatives over the prior art by providing a female urine device that is composed of a shell portion and a spout portion. The shell portion forms a trough shaped inner chamber. The spout portion may extend from a forward opening in the shell portion. The shell portion may include thumb tabs to enable a female to easily leverage the urine device into sealing engagement with the female's genitalia without collapsing. The shell portion may include an upper rim with a concave shaped designed for a comfortable anatomical fit against the female's genitalia when in use. The spout portion may have an extended position that is long enough to direct urine away from the body without splashing onto a female's clothing. The spout portion may have at least one folded position that enables the female urine device to be more compactly stored. The spout portion may be phosphorescent to enable a female to see the female urine device in the dark and to provide an illuminated directional pointer to direct the urine in a given direction.

A female urine device in accordance with one or more aspects of the present disclosure includes a shell portion and a spout portion. The shell portion includes a bottom wall, a first sidewall, a second sidewall and a rear wall integrally connected to define a trough shaped inner chamber. A forward opening is defined by forward ends of the walls. An upper rim is defined by upper ends of the walls. The spout portion extends forward from the forward opening of the shell portion. A portion of the female urine device is phosphorescent.

An alternative female urine device in accordance with one or more aspects of the present disclosure includes a shell portion, a spout portion and at least one thumb rest. The shell portion includes a bottom wall, a first sidewall, a second sidewall and a rear wall integrally connected to define a trough shaped inner chamber. A forward opening is defined by forward ends of the walls. An upper rim is defined by upper ends of the walls. The spout portion extends forward from the forward opening of the shell portion. At least one thumb rest is disposed on a sidewall of the shell portion and extends perpendicularly therefrom. The at least one thumb rest is disposed adjacent to the forward opening of the shell portion. The at least one thumb rest is sized to receive a thumb of a female and is operable as a fulcrum to enable the female to leverage the rim of the shell portion into sealing engagement with the female's genitalia when the female urine device is in use.

A method of making a female urine device in accordance with one or more aspects of the present disclosure includes providing a base material for a shell portion and a spout portion of a female urine device. Phosphorescent material is added to the base material. The base material is thermally molded to form a female urine device. The female urine device includes a shell portion and a spout portion. The shell portion includes a bottom wall, a first sidewall, a second sidewall and a rear wall integrally connected to define a trough shaped inner chamber. The shell portion also includes a forward opening defined by forward ends of the walls and an upper rim defined by upper ends of the walls. The spout portion extends forward from the forward opening of the shell portion. A portion of the female urine device is phosphorescent.

DRAWINGS

The disclosure will be more fully understood from the following detailed description taken in conjunction with the accompanying drawings, in which:

FIG. 7 depicts a perspective view of an example of a female urine device with its spout portion in a folded position within an inner chamber of the female urine device, according to aspects described herein;

FIG. 8 depicts a perspective view of an example of a female urine device with its spout portion in a folded position against a bottom wall of the female urine device, according to aspects described herein;

FIG. 10A depicts an example of a flow diagram of a method of making a female urine device, according to aspects described herein; and FIG. 10B depicts an example of a flow diagram of a continuation of the method of making a female urine device of FIG. 10A, according to aspects described herein.

DETAILED DESCRIPTION

Certain examples will now be described to provide an overall understanding of the principles of the structure, function, manufacture, and use of the methods, systems, and devices disclosed herein. One or more examples are illustrated in the accompanying drawings. Those skilled in the art will understand that the methods, systems, and devices specifically described herein and illustrated in the accompanying drawings are non-limiting examples and that the scope of the present disclosure is defined solely by the claims. The features illustrated or described in connection with one example may be combined with the features of other examples. Such modifications and variations are intended to be included within the scope of the present disclosure.

The terms "substantially", "approximately", "about", "relatively," or other such similar terms that may be used throughout this disclosure, including the claims, are used to describe and account for small fluctuations, such as due to variations in processing from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Figure 9A:
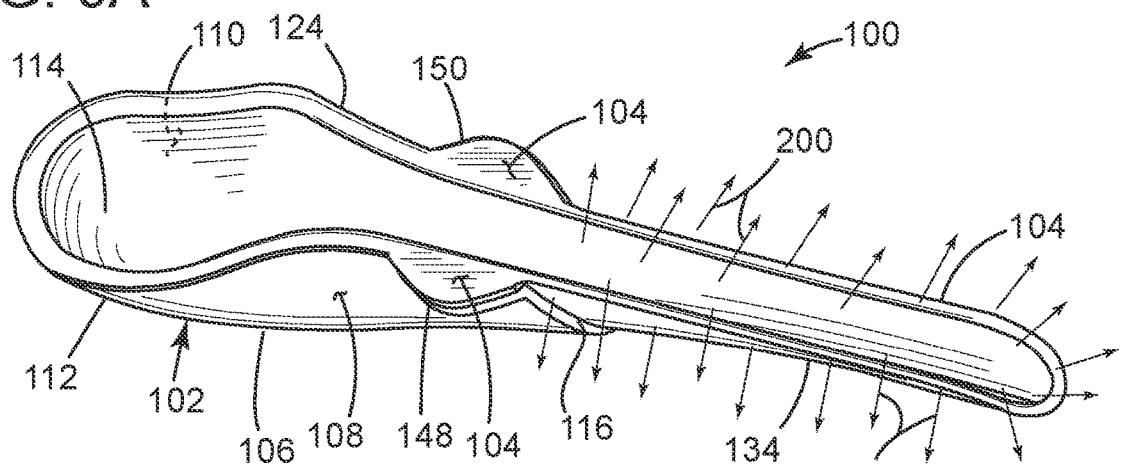
FIG. 9A depicts a perspective view of an example of a female urine device with a shell portion and a spout portion, wherein the spout portion is phosphorescent, according to aspects described herein.
Figure 9B:
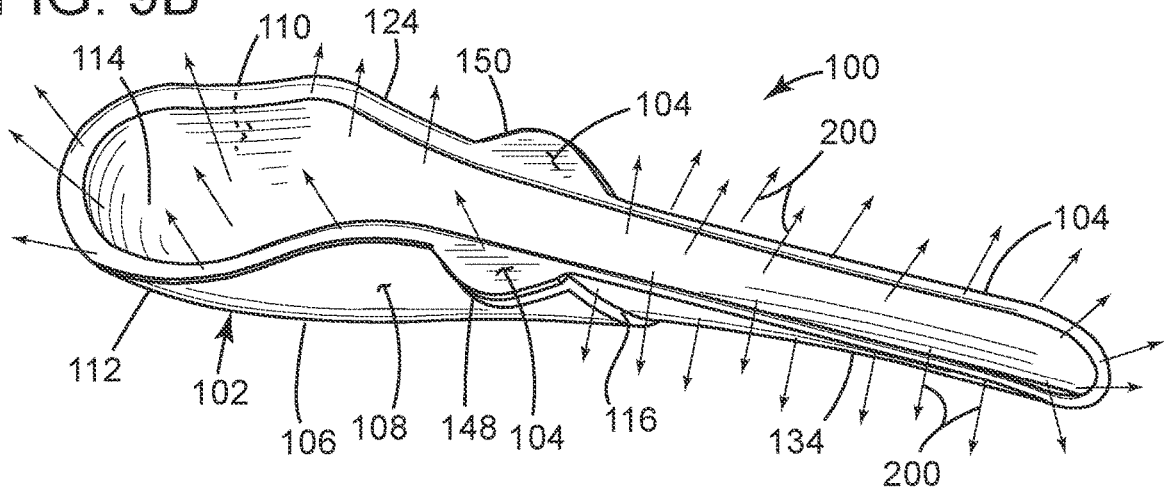
FIG. 9B depicts a perspective view of an example of female urine device with a shell portion and an inner liner, the inner liner including a spout portion, wherein the entire inner liner is phosphorescent, according to aspects described herein.
Figure 9C:
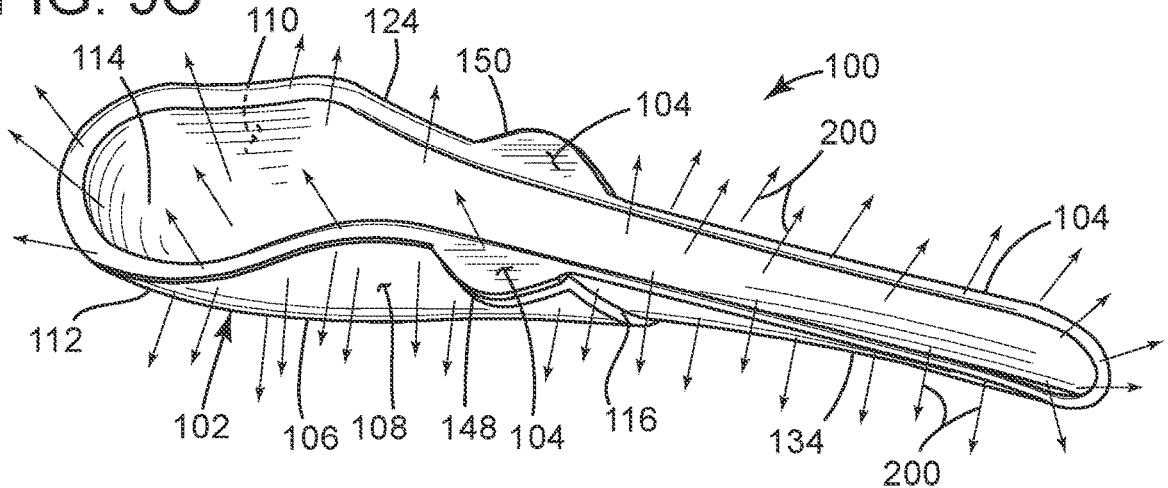
FIG. 9C depicts a perspective view of an example of a female urine device, wherein the entire female urine device is phosphorescent, according to aspects described herein.

FIGS. 1-4 illustrate various examples of a female urine device in an extended position according to aspects described herein. FIG. 5 illustrates an example of a female urine device having thumb rests operable as fulcrums to enable a female to leverage the device into an anatomic sealing engagement with the female's genitalia according to aspects described herein. Finally, FIGS. 7-8 illustrate various examples of a female urine device in at least one folded position according to aspects described herein. FIGS. 9A-9C illustrate examples of a female urine device, wherein various portions of the device are phosphorescent. FIGS. 10A-10B illustrate an example of a method of making a female urine device.

Referring to FIGS. 1-4, a perspective view (FIG. 1), a top view (FIG. 2), a bottom view (FIG. 3) and a side view (FIG. 4) of an example of a female urine device 100 is presented according to aspects described herein. The urine device 100 includes a shell (or shell portion) 102 and a resilient liner 104.

Figure 1:
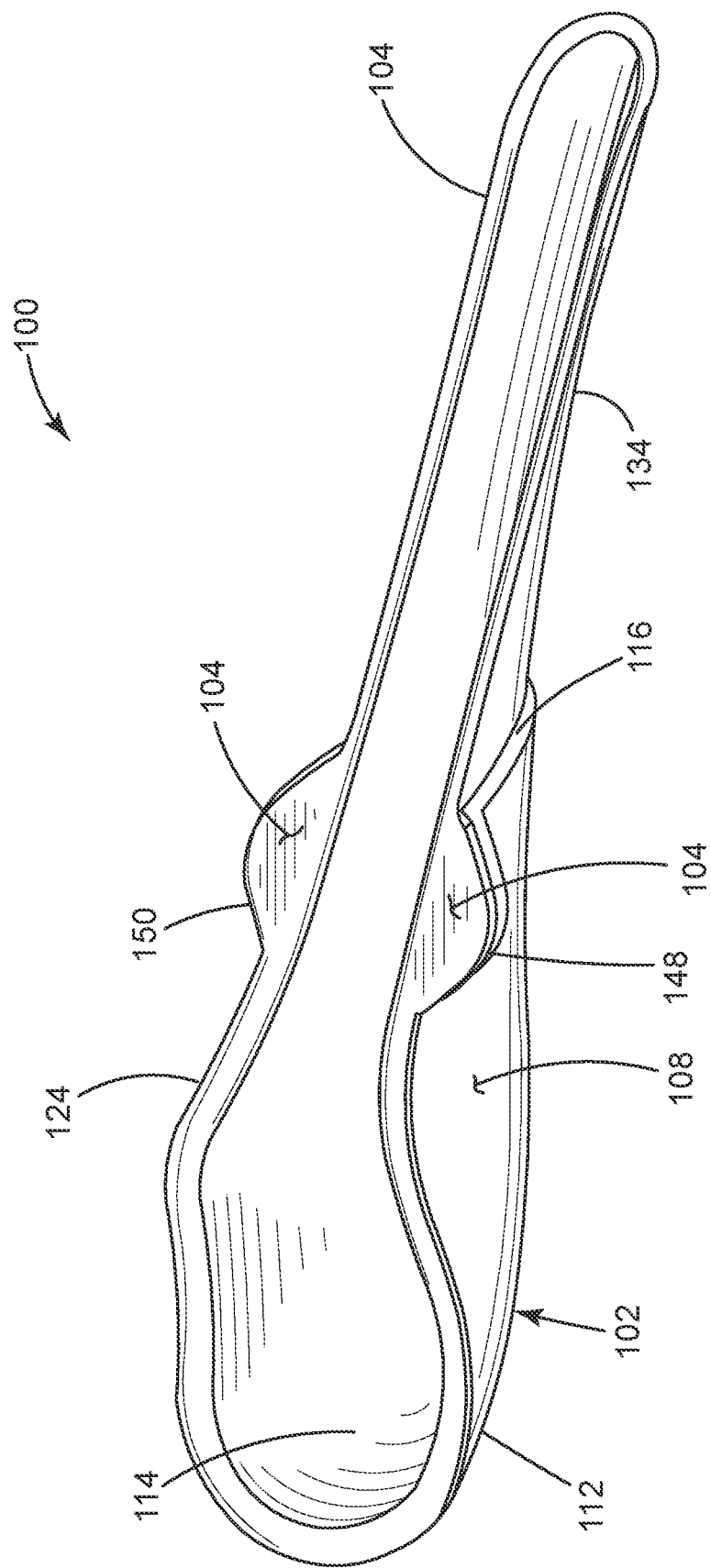
FIG. 1 depicts a perspective view of an example of a female urine device having a shell and an inner liner, wherein the inner liner includes a spout portion that is in an extended position, according to aspects described herein.
Figure 2:
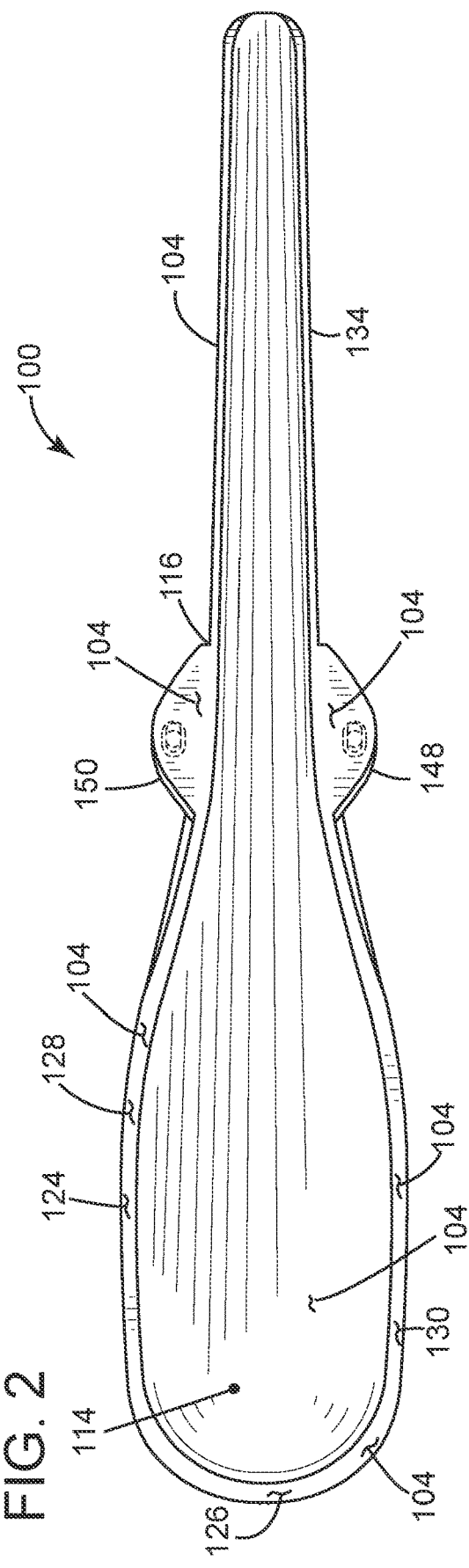
FIG. 2 depicts a top view of the example of the female urine device of FIG. 1, according to aspects described herein.
Figure 3:
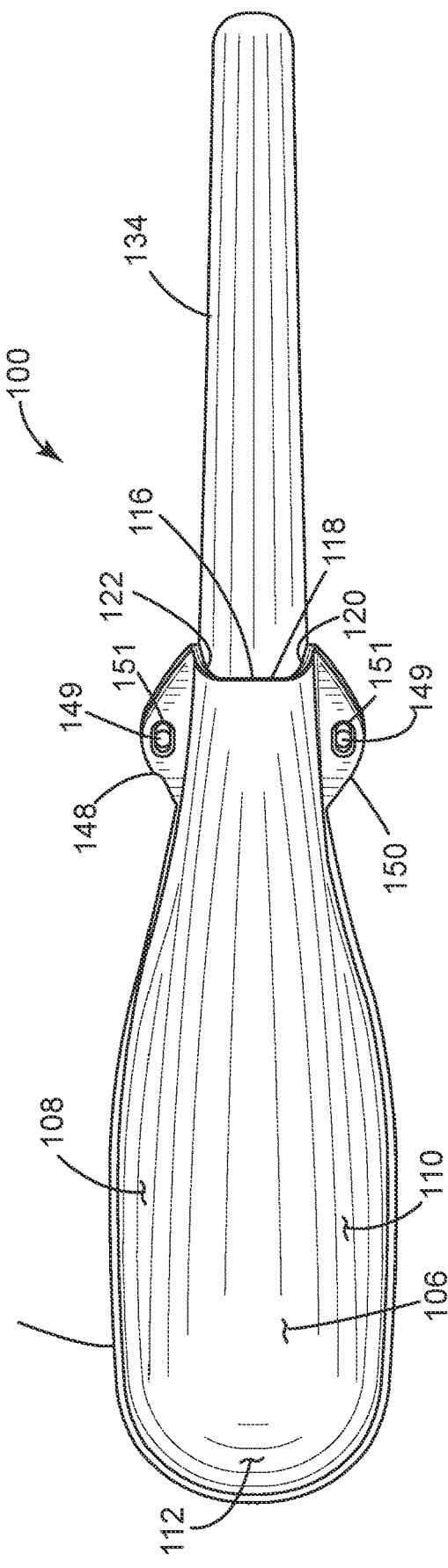
FIG. 3 depicts a bottom view of the example of the female urine device of FIG. 1, according to aspects described herein.
Figure 4:
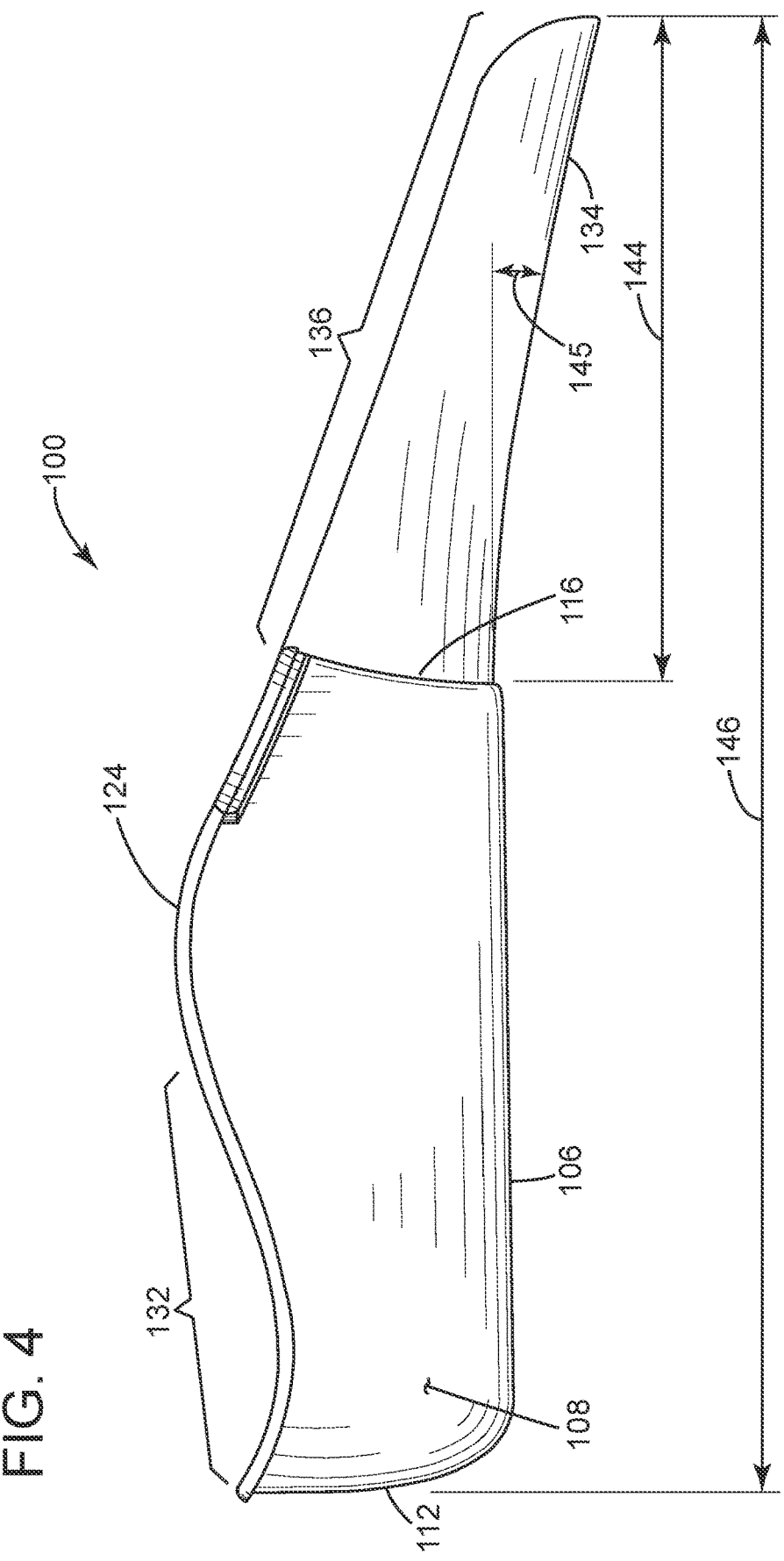
FIG. 4 depicts a side view of the example of the female urine device of FIG. 1, according to aspects described herein.

The shell portion 102 includes a bottom wall 106, a first sidewall 108, a second sidewall 110 and a rear wall 112 (the walls being best seen in FIG. 3). The walls 106, 108, 110, 112 are integrally connected together to define a trough shaped inner chamber 114 (best seen in FIG. 2).

The shell 102 includes a generally U-shaped forward opening 116. The opening 116 is defined by a forward end 118 of the bottom wall 106, a forward end 120 of the first sidewall 108 and a forward end 122 of the second sidewall 110 (best seen in FIG. 3).

The shell portion 102 also includes an upper rim 124. The rim 124 is defined by an upper end 126 of the rear wall 112, an upper end 128 of the first sidewall 108 and an upper end 130 of the second sidewall 110 (best seen in FIG. 2). As will be discussed in greater detail herein, a portion of the rim 124 includes a concave shaped curve 132 (best seen in FIG. 4) that is designed to anatomically fit against a female's genitalia. More specifically, the rim 124 includes a pair of concave shaped curves 132 that are disposed along a portion of the upper ends 128, 130 of each sidewall 108, 110 respectively.

The shell portion 102 may be tough enough such that it will not collapse during use. More specifically, it will not collapse when enough pressure is applied to the shell to assure a leak proof fit with a female's genitalia during use.

Moreover, the shell 102 may be tough in that it may have the quality of being strong or firm in texture, but flexible and not brittle. Accordingly, the shell portion may be flexible enough to allow a female user to spread the upper ends 128 of the first side wall 108 and the upper end 130 of the second side wall 110 apart in order to customize the fit of the female urine device 100 to different body types when in use. Additionally, the shell portion may be durable enough such that it will resist cracking when inadvertently stepped on or dropped. When used, the trough shaped inner chamber 114 of the shell 102 is sized to fit over a female's urethra (including a female's urethral orifice) and to receive urine therefrom without spillage.

The shell portion 102 may be composed of a variety of materials. For example, the shell portion 102 may be composed of a non-absorbent plastic such as polypropylene, metal, glass, carbon, cellulose, ceramic, biodegradable material or the like. Additionally, the shell portion 102 may be impregnated with anti-microbial additives to reduce the potential for bacterial growth in the liner. Further, the shell portion 102 may be impregnated with ultraviolet (UV) stabilizer additives to help prevent device degradation. Also, hydrophobic additives may be impregnated into the shell portion 102 to help make the shell non-porous or to enhance the shell's properties to shed liquids. Also, as will be explained in greater detail herein, the shell portion 102 may be impregnated with phosphorescent materials that enable a user to visualize the female urine device in the low light conditions to facilitate use in the event no light is present.

The resilient liner 104 is disposed on, and may cover, the entire inner chamber 114 (best seen in FIG. 2). The liner 104 also may cover the upper rim 124 of the shell 102. The liner 104 extends forward past the forward opening 116 of the shell 102 to form a spout portion 134 of the liner 104.

Though the shell portion 102 and liner 104 are often different materials, they may also be composed of the same material. For example, both shell portion 102 and liner 104 may be composed of polypropylene, wherein neither the shell portion 102 nor the liner are resilient. Alternatively, both the shell portion 102 and the liner 104 may be composed of a thermo plastic elastomer, wherein both the shell portion 102 and the liner 104 are resilient.

Moreover, the liner 104 may not cover the entire inner chamber 114. Rather the liner 104 may include the spout portion 134 of the liner only, wherein the spout portion 134 extends forward from the forward opening 116 of the shell portion 102.

As will be discussed in greater detail herein, the spout portion 134 may have an extended position and may have at least one folded position. More specifically, the spout portion 134 may have an extended position 136 (best seen in FIG. 4) that the spout portion 134 is positioned in when the female urine device 100 is in use. Also, more specifically for the examples illustrated herein, the spout portion 134 may have at least three folded positions 190, 192, 194 (best seen in FIGS. 6, 7, and 8 respectively) that the spout portion 134 may be positioned in when the female urine device 100 is being stored.

When the spout portion 134 is in its extended position 136, the spout portion 134 may have a length 144 that is greater than 40% of an extended length 146 of the female urine device 100. The reason that the length 144 of the spout portion 134 in its extended position 136 can be so long relative to the extended length 146 of the device 100, is that the shell portion 102 supports the spout portion 134 of the liner 104.

As such, the spout portion 134 may be advantageously resilient and flexible enough to be folded into a variety of folded positions 190, 192, 194 for compact storage. However due in no small part to the added support of the shell portion 102, the spout portion 134 is also advantageously rigid enough in its extended position 136 to direct urine flow well away from a female's body without splashing urine on a female's clothing. For example, if a female urine device 100 is designed to have an overall length of about 9 inches, the spout portion 134 may be up to 4 inches long and longer in its extended position 136 in order to direct urine 178 away from the body 160 when in use (best seen in FIG. 5B).

Additionally, when the spout portion 134 is in its extended position 136, the floor of the spout portion 134 forms a downward sloping angle 145 relative to the bottom wall 106 of the shell portion 102. The downward sloping angle 145 is preferably within a range of about 5 degrees to 20 degrees. More preferably the angle 145 is within a smaller range of about 10 degrees to 15 degrees. The downward sloping angle 145 aids in directing the urine flow down and away from a female's body without splashing urine on a female's clothing.

The resilient liner 104 may be composed of a variety of materials. For example, the liner 104 may be composed of a non-absorbent, non-porous plastic, urethane, cellulose, carbon, silicone, rubber, biodegradable material, a thermo plastic elastomer (TPE) or the like. Additionally, the liner 104 may be impregnated with anti-microbial additives to reduce the potential for bacterial growth in the liner. Further, the liner 104 may be impregnated with ultraviolet (UV) stabilizer additives to help prevent degradation. Also, hydrophobic additives may be impregnated into the liner 104 to help make the liner non-porous or to enhance the shell's properties to shed liquids. Further, the liner may be impregnated with phosphorescent material such as phosphor, zinc sulfide, strontium aluminate or the like material/chemical composition.

At least one thumb rest 148 may be disposed on a sidewall 108 of the shell portion 102 and extend perpendicularly therefrom. As will be discussed in greater detail herein, the at least one thumb rest 148 is sized to receive a thumb (or other digit if appropriate) of a female and is advantageously operable as a fulcrum to enable the female to leverage the rim 124 of the shell portion 102 into sealing engagement with the female's genitalia when the female urine device 100 is in use. Moreover, the additional surface area of the thumb rest 148 provides comfort to the user's finger when applying pressure.

More specifically for the examples illustrated herein, there is a pair of first 148 and second 150 thumb rests, wherein the first thumb rest 148 is disposed on the first sidewall 108 and the second thumb rest 150 is disposed on the second sidewall 110. The pair of thumb rests 148, 150 may be disposed on the rim 124 and may be adjacent the forward opening 116 of the shell portion 102. The pair of thumb rests 148, 150 may be composed of the same material as that of the shell portion 102.

The liner 104, as illustrated in these examples, may also cover the thumb rests 148, 150 (best seen in FIG. 2). This has the advantageous effect of providing a more comfortable and non-slip surface relative to the material of the shell portion 102. As such, the thumb of a female would be less prone to slipping off of the thumb rests 148, 150 during use.

Additionally, the thumb rests 148, 150 act as a reference guide for consistent proper placement against a female's body. More specifically (as best seen in FIG. 5B), when the female urine device 100 is in use, the thumb rests 148, 150 are positioned on the forward end of the shell portion 102 and the shell portion 102 is sized such that when the thumb rests 148, 150 are in front of (or anterior to) a female's body, the rear wall 112 of the shell portion 102 is positioned behind (or posterior to) the urethral orifice 176.

In this specific example, the liner 104 includes a pair of tabs 149 (best seen in FIG. 3) that extend downward into through-holes 151 that are disposed in the thumb rests 148, 150. The tabs 149 help to properly position the liner 104 relative to the tabs 148, 150 and the shell portion 102. The tabs 149 also help to further fix the position of the liner 104 against the thumb rests 148, 150 during use of the female urine device 100.

Figure 5A:
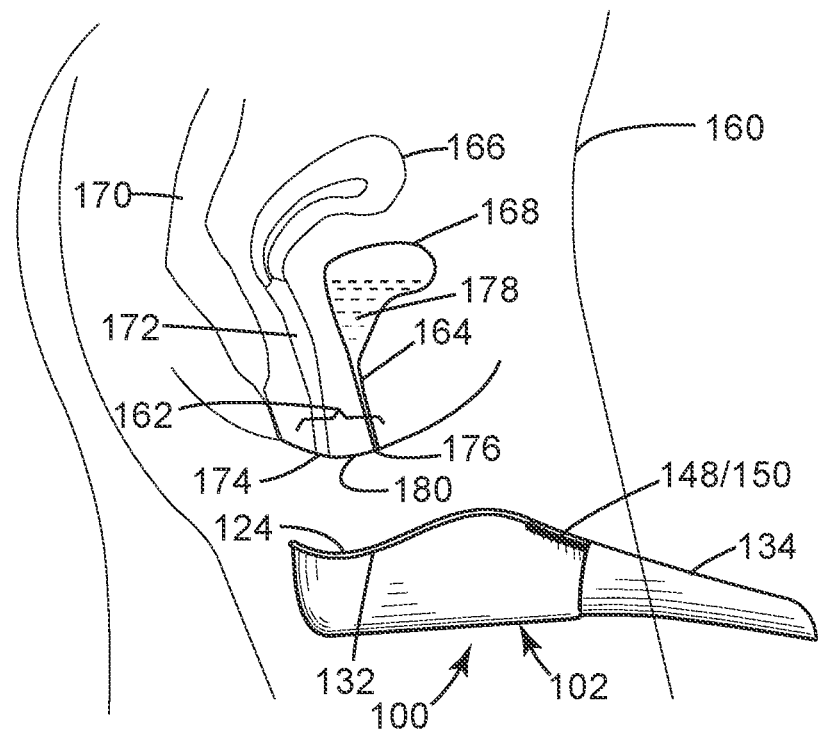
FIG. 5A, depicts a perspective view of an example of a female urine device positioned such that it is about to be engaged against a female's body, according to aspects described herein.
Figure 5B:
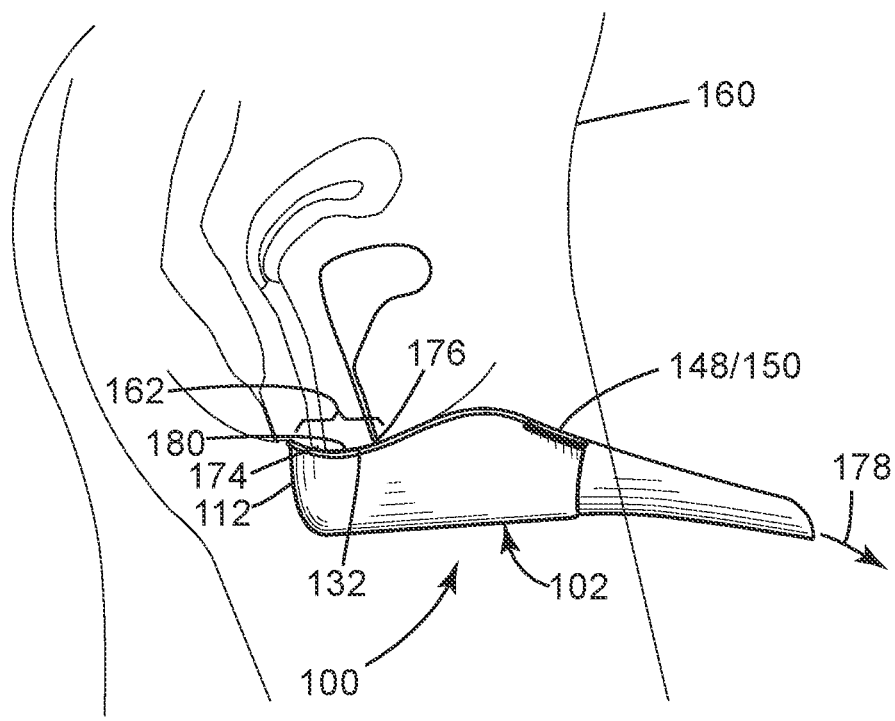
FIG. 5B depicts a perspective view of an example of the female urine device of FIG. 5A positioned against a female's body, according to aspects described herein.

Referring to FIG. 5A, a perspective view of an example of the female urine device 100 positioned such that it is about to be engaged against a female's body 160 according to aspects described herein is presented. The shell portion 102 of the female urine device 100 is sized such that when the upper rim 124 is engaged with the female's genitalia 162, the liner covered inner chamber 114 (best seen in FIG. 1) is positioned to receive urine from the female's urethral orifice 176 and the pair of thumb rests 148, 150 are positioned in front of (or anterior to) the female's body 160.

The female uterus 166 is the hollow muscular organ positioned in the female's body 160 between the bladder 168 and rectum 170 and is part of the female's reproductive system. The uterus 166 connects through the vaginal canal 172 to the vaginal opening 174, which is part of the female's external genitalia 162.

The urethral orifice 176 is positioned anterior to (or in front of) the vaginal opening 174. Urine 178 is stored in the bladder 168 and flows through the urethra 164, where it is ejected out of the urethral orifice 176 during urination.

The area of a female's body which includes the female's genitalia 162 forms a convex shaped curvature 180 due, in large part, to the shape of the female's pelvis (not shown). The concave curve 132 of the female urine device 100 is designed to anatomically fit against the convex curvature 180 of the female's body 160 to provide a more comfortable fit and to enable a leak resistant seal with minimal pressure. Moreover, the thumb rests 148, 150 are positioned forward of the concave curve 132 so that the thumb rests 148, 150 do not interfere with the fit of the concave curve 132 to the convex curvature 180 of female's genitalia 162.

By way of example, the concave curve 132 may have a radius of curvature that is within a range of 2.0 inches to 3.25 inches. More preferably the concave curve 132 may have a radius of curvature that is within a smaller range of 2.15 inches to 2.85 inches. These examples of ranges of radii will, in most cases, enable the female urine device 100 to anatomically fit against the corresponding convex curvature 180 of the female's body 160.

Additionally, by way of example, the concave shaped curve 132 may form an arc that is within an angular range of between 25 degrees and 60 degrees. More preferably, the curve 132 may form an arc that is within an angular range of between 40 degrees and 60 degrees.

Referring to FIG. 5B, a perspective view of an example of the female urine device 100 positioned against a female's body 160 according to aspects described herein is presented. When the urine device 100 is in use, the upper rim 124 is operable to engage a female's genitalia 162. The liner covered inner chamber 114 (best seen in FIG. 1) is operable to receive urine 178 from the female's urethral orifice 176. Further, the spout portion 134 is in an extended position 136 to direct the urine 178 away from the female's body 160.

To engage the female urine device 100 during use, a female may use the thumb rests 148, 150 as reference points in front of the female's body 160 to properly position the device 100. For example, the thumb rests 148, 150 may be positioned on the shell portion 102 proximate its forward opening 116 and forward of its concave curve 132. The shell portion 102 may be sized such that, when a female positions the thumb rests 148, 150 in front of her body, the rear wall 112 of the shell portion 102 will be located behind her urethral orifice and the concave curve 132 will anatomically fit against the convex curve 180 of the female's genitalia 162. The liner covered inner chamber 114 of the shell portion 102 is placed under the urethral orifice 176, so that urine 178 flows directly into the chamber 114. When so placed, the rim 124 on the upper end of the rear wall 112 is generally positioned under, or near, the vaginal opening 174 and the thumb rests 148, 150 are accessible in front of the female's clothing.

By placing her thumbs (not shown) on the thumb rest 148, 150 and cupping the bottom wall 106 of the shell 102 with her fingers (not shown), a female may utilize the thumb rests 148, 150 as a fulcrum to leverage the rim 124 of the shell portion 102 into sealing engagement with the female's genitalia 162. Accordingly, the rim 124 on the rear wall 112 is pushed upwards to seal against the genitalia 164 while the spout portion 134 is pushed downward to aim the flow of urine 178 away from the body 160. Advantageously, the proportionally long length 144 of the spout portion 134 in its extended position 136 (e.g., more than 40% of the extended length 146 of the female urine device 100) enables the flow of urine 178 to be directed away from the female's body without inadvertently splashing on her clothing. Additionally, the presence of hydrophobic additives enhances the device's ability to not absorb any urine and to shed the urine more quickly.

When the urination process is completed, the rim 124 on the upper end of the rear wall 112 of the female urine device 100 is operable to act like a squeegee device to wipe the genitalia 162 clean of urine. This may be accomplished by gently pulling the female urine device 100 forward (or anteriorly) while maintaining pressure of the rim 124 of the rear wall 112 against the body 160. The soft resilient liner 104 covering the rear wall rim 124 will wipe urine off of the genitalia 162 in a squeegee like fashion. The remaining drops of urine may then be shaken off of the urine device 100. Additionally, the antimicrobial additives (which for example may be silver based) that have been impregnated into the liner 104 will work to reduce the potential for bacterial growth on the liner 104 during and after the process of wiping the female genitalia 162.

Figure 6:
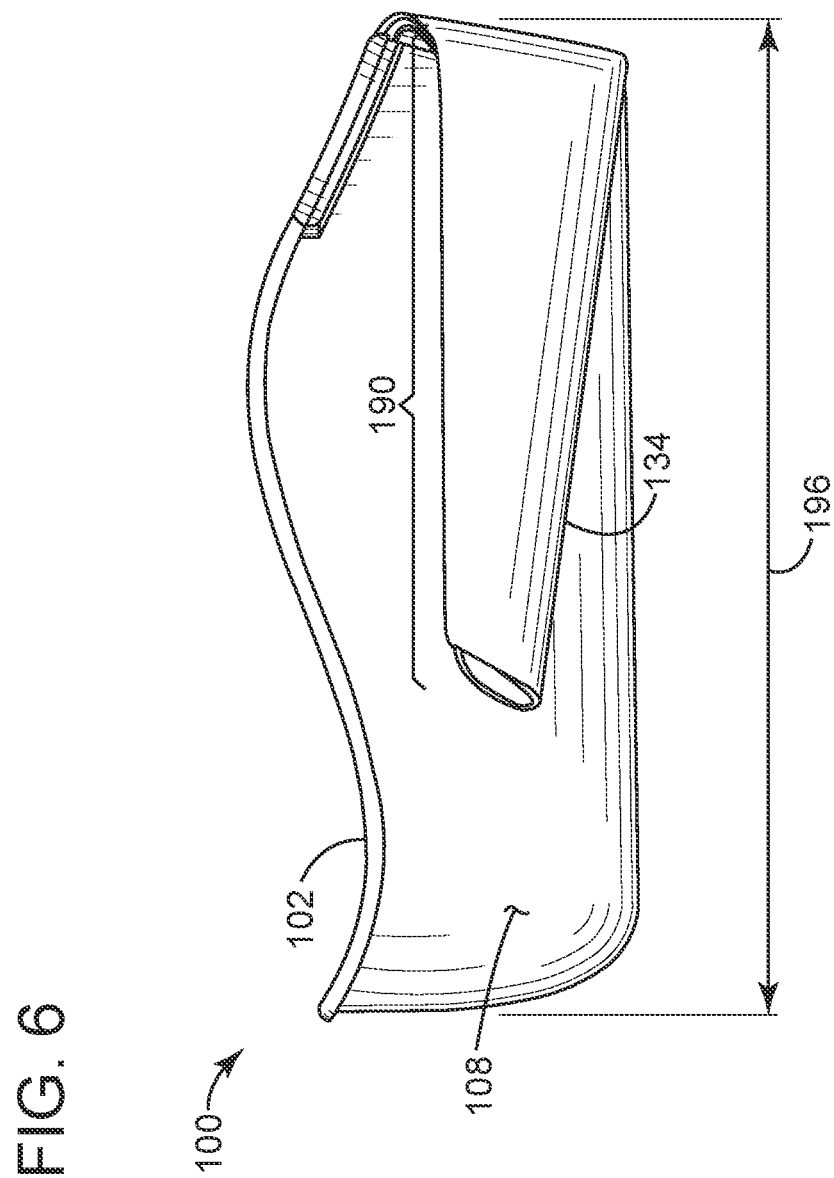
FIG. 6 depicts a perspective view of an example of a female urine device with its spout portion in a folded position against a sidewall of the female urine device, according to aspects described herein.

Referring to FIGS. 6, 7 and 8, various examples of a female urine device 100 with its spout portion 134 in a folded position are presented according to aspects described herein. More specifically, FIG. 6 depicts a perspective view of an example of a female urine device 100 with its spout portion 134 in a first folded position 190 against a sidewall 108 of the female urine device 100. Also, FIG. 7 depicts a perspective view of an example of a female urine device 100 with its spout portion 134 in a second folded position 192 within an inner chamber 114 of the female urine device 100. Further, FIG. 8 depicts a perspective view of an example of a female urine device 100 with its spout portion 134 in a third folded position 194 against a bottom wall 106 of the female urine device 100. The various folded positions 190, 192, 194 enable the female urine device 100 to advantageously be more compactly stored when not in use.

When the urine device 100 is not in use, the spout portion 100 is operable to be folded into at least one folded position 190, 192, 194 against the shell portion 102 for purposes of storage of the urine device. When the spout portion 134 is in its folded position 190, 192, 194, the female urine device 100 has a folded length 196 that is less than 67% of its extended length 146.

The reason that the folded length 196 is small relative to the extended length 146 (e.g., less than 67% of the extended length 146) of the urine device 100 is because of the resiliency and the proportionally long length 144 of the spout portion 134. That is, the resiliency of the spout portion 134 allows it to be folded against the shell portion 102. Further, the proportionally long length of the spout portion 134 enables a significant difference between the extended length 136 and folded length 196 of the device 100. For example, if a female urine device 100 is designed to have an overall length of about 9 inches, the spout portion 134 may be up to 4 inches long and longer in order to direct urine away from the body when in use. However, when the spout portion 134 is folded against the shell portion 102, the folded length will be reduced to about 5.5 inches. Accordingly, the female urine device 100 will be long enough to prevent urine from splashing onto a females clothing when in use, but will also be very compact for storage when not in use.

Referring to FIG. 6, more specifically, an example of the female urine device 100 with its spout portion 134 in the first folded position 190 against a sidewall 108, 110 of the female urine device 100 is illustrated. The spout portion 134 may be folded against either the first side wall 108 or the second side wall 110.

Referring to FIG. 7, more specifically, an example of the female urine device 100 with its spout portion 134 in a second folded position 192 within the liner covered inner chamber 114 of the female urine device 100 is illustrated. The spout portion 134 may be fully enclosed within the inner chamber 114.

Referring to FIG. 8, more specifically, an example of the female urine device 100 with its spout portion 134 in the third folded position 194 against the bottom wall 106 of the female urine device 100 is illustrated. Advantageously, when the spout portion 134 is folded against the bottom wall 106, the spout portion 134 alone is operable to retain itself in its folded position 194 without snapping back into its extended position 136. Though three folded positions 190, 192, 194 of the spout portion 134 have been illustrated therein, other folded positions may also be used to reduce the overall length of the female urine device 100 when not in use.

Referring to FIGS. 9A, 9B and 9C, examples are depicted of perspective views of a female urine device with a shell portion 102 and a spout portion 134, wherein various portions of the female urine device 100 are phosphorescent, wherein they emit a photoluminescent light 200. More specifically, FIG. 9A depicts an example of a perspective view of a female urine device 100, wherein the spout portion 134 is photoluminescent. FIG. 9A depicts an example of a perspective view of a female urine device 100, wherein the liner 104 is photoluminescent. FIG. 9C depicts an example of a perspective view of a female urine device 100, wherein the entire female urine device is photoluminescent, including the shell portion 102 and the liner 104 with the liner's spout portion 134.

The female urine device 100 of FIGS. 9A, 9B and 9C may include at least a shell portion 102 and a spout portion 134. The shell portion 102 may include a bottom wall 106, a first sidewall 108, a second sidewall 110 and a rear wall 112 integrally connected to define a trough shaped inner chamber 114. A forward opening 116 is defined by forward ends of the walls 106, 108, 110. An upper rim 124 is defined by upper ends of the walls 108, 110, 112. The spout portion 134 extends forward from the forward opening 116 of the shell portion 102. A portion of the female urine device is phosphorescent, for example, the spout portion 134, the entire inner liner 104 and/or the shell portion 102.

The female urine device 100 of FIGS. 9A, 9B and 9C may also include the upper rim 124, which extends from an upper end of the rear wall 112 to the forward opening 116. The forward opening 116 may define an open end of the upper rim 124. A resilient liner 104 may be disposed on the inner chamber 114, wherein the liner 104 may extend forward past the forward opening 116 of the shell portion 102 to form the spout portion 134.

The female urine device 100 of FIGS. 9A, 9B and 9C may also include at least one thumb rest (and preferably a pair of thumb rests 148, 150) disposed on a sidewall of the shell portion 102 and extending perpendicularly therefrom. The at least one thumb rest 148, 150 may be disposed adjacent to the forward opening 116 of the shell portion 102. The at least one thumb rest 148, 150 may be sized to receive a thumb of a female and be operable as a fulcrum to enable the female to leverage the rim 124 of the shell portion 102 into sealing engagement with the female's genitalia when the female urine device 100 is in use.

Though the shell portion 102, liner 104 and spout portion 134 of the liner are illustrated in FIGS. 9A-9C as being composed of different materials (for example, the shell portion 102 may be polypropylene and the liner 104 with its spout portion 134 may be an elastomer), they may also be composed of the same material. For example, both shell portion 102, liner 104 and spout portion 134 may be composed of polypropylene, wherein neither the shell portion 102 nor the liner 104 with its spout portion 134 are resilient. Alternatively, each of the shell portion 102, liner 104 and the spout portion 134 of the liner 104 may be composed of a thermo plastic elastomer, wherein each of the shell portion 102, the liner 104 and the spout portion 134 are resilient.

Photoluminescent/phosphorescent materials may be added to any portion of the female urine device 100 to give the device 100 its glow-in-the-dark characteristics. For example, phosphorescent material may be added to the either the shell portion 102, the liner 104 and/or the spout portion 134 during manufacture. The phosphorescent material may be a phosphor, zinc sulfide, strontium aluminate or the like.

Moreover, the phosphorescent material may be a compound. The main material in the phosphorescent material compound may be phosphor. Materials in the phosphor may include strontium aluminum, europium, dysprosium in varying proportions with strontium aluminum being the main ingredient.

The phosphorescent material is often in pellet or powder form that that may be blended into the base material(s) in the manufacturing method of the female urine device 100. However, the phosphorescent material may be painted on as well.

The phosphorescent material may be added into the base material (e.g., polypropylene or thermo plastic elastomer) of the shell portion 102, the liner 104 and/or the spout portion 134 by a percentage of weight. For example, the phosphorescent material may be between 1 to 25 percent of the base material by weight. Also, for example, the phosphorescent material may be between 3 to 12 percent by weight of the base material by weight.

By making portions of the female urine device 100 phosphorescent, the female urine device 100 may be more easily used in a low light setting, which would be advantageous to a user in such circumstances. Even more advantageous is if the spout portion 134 is made phosphorescent, in this case the spout portion 134 acts as a glowing line-of-sight indicator, that can show the user where the urine stream is being directed even in the absence of any other light. Since many people use two hands to urinate with female urine devices, holding a light or other illumination device at the same time that they are directing the urine stream in a low light situation may be problematic. Having the spout portion 134 phosphorescent facilitates the use of the device.

Referring to FIG. 10A, an example is depicted of a flow diagram of a method of making a female urine device, according to aspects describe herein. The method begins at 202, wherein a base material is provided for at least a shell portion 102 and a spout portion 134 of a female urine device 100. There may also be provided a base material to include a liner 104 and a pair of thumb rests 148, 150.

At 204, phosphorescent material is added to the base material. The phosphorescent material may be composed of at least one of phosphor, zinc sulfide, strontium aluminum, europium or dysprosium. Moreover, the phosphorescent material may be a compound. The main material in the phosphorescent material compound may be phosphor. Materials in the phosphor may include strontium aluminum, europium, dysprosium in varying proportions with strontium aluminum being the main ingredient. The base material may be composed of polypropylene or a thermo plastic elastomer.

At 206, the base material may be thermally molded to form the female urine device 100, wherein the female urine device 100 includes the shell portion 102 and the spout portion 134. The shell portion 102 may include a bottom wall 106, a first sidewall 108, a second sidewall 110 and a rear wall 112 integrally connected to define a trough shaped inner chamber 114. The shell portion 102 may also include a forward opening 116 defined by forward ends of the walls and an upper rim 124 defined by upper ends of the walls. The spout portion 134 extends forward from the forward opening 116 of the shell portion 102. A portion of the female urine device 100 is phosphorescent. The phosphorescent portion may be the spout portion 134.

Referring to FIG. 10B, an example is depicted of a flow diagram of a continuation of the method of making a female urine device 100 of FIG. 10A, according to aspects described herein. The method continues at 208, wherein the phosphorescent material may be in pellet or powder form and may be added to the base material prior to thermally molding the base material to form the female urine device 100. Alternatively, the phosphorescent material may be painted onto the female urine device 100 after the female urine device 100 has been thermally molded.

At 210, if the phosphorescent material is blended into the base material prior to thermally molding the base material, then the phosphorescent material may be blended into the base material in a range of between 1 to 25 percent of the base material by weight. Moreover, the phosphorescent material may be blended into the base material in a range of between 3 to 12 percent of the base material by weight.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

What is claimed is:

1. A female urine device, comprising:
a shell portion comprising:
a bottom wall, a first sidewall, a second sidewall and a rear wall integrally connected to define a trough shaped inner chamber,
a forward opening defined by forward ends of the walls, and
an upper rim defined by upper ends of the walls; and
a spout portion extending forward from the forward opening of the shell portion;
wherein the entire spout portion is phosphorescent such that the spout portion is operable to direct a urine stream away from a female user's body and act as a glowing line-of-sight indicator that shows the female user the direction of the urine stream while the female user is standing.

2. The female urine device of claim 1, wherein the entire female urine device is phosphorescent.

3. The female urine device of claim 1, further comprising:
the upper rim extending from an upper end of the rear wall to the forward opening, wherein the forward opening defines an open end of the upper rim; and
a resilient liner disposed on the inner chamber, the liner extending forward past the forward opening of the shell portion to form the spout portion;
wherein the entire liner is phosphorescent.

4. The female urine device of claim 1, further comprising:
at least one thumb rest disposed on a sidewall of the shell portion and extending perpendicularly therefrom, the at least one thumb rest being disposed adjacent to the forward opening of the shell portion, the at least one thumb rest sized to receive a thumb of a female and being operable as a fulcrum to enable the female to leverage the rim of the shell portion into sealing engagement with the female's genitalia when the female urine device is in use.

5. The female urine device of claim 4, wherein the at least one thumb rest is a pair of first and second thumb rests, wherein the first thumb rest is disposed on the first sidewall and the second thumb rest is disposed on the second sidewall.

6. The female urine device of claim 5, wherein the pair of thumb rests are disposed on the rim and are adjacent the forward opening of the shell portion.

7. The female urine device of claim 3, wherein:
when the urine device is in use, the upper rim is operable to engage a female's genitalia, the liner covered inner chamber is operable to receive urine from the female's urethral orifice and the spout portion is in an extended position to direct the urine away from the female's body; and
when the urine device is not in use, the spout portion is operable to be folded into at least one folded position against the shell portion for purposes of storage of the urine device.

8. The female urine device of claim 7, wherein the at least one folded position of the spout portion comprises a folded position, wherein the spout portion is disposed against the bottom wall of the urine device while the resilient liner remains disposed on the inner chamber.

9. The female urine device of claim 1, wherein a portion of the upper rim has a concave shaped curve designed to anatomically fit against the female's genitalia.

* * * * *